United States Patent
Pinappu et al.

(10) Patent No.: US 11,491,466 B2
(45) Date of Patent: Nov. 8, 2022

(54) ETHYLENEAMINES FOR REGENERATING ADSORBENT BEDS FOR SULFUR COMPOUND REMOVAL

(71) Applicant: Baker Hughes Oilfield Operations LLC, Houston, TX (US)

(72) Inventors: Sai Reddy Pinappu, Sugar Land, TX (US); Jerry J. Weers, Richmond, TX (US)

(73) Assignee: Baker Hughes Oilfield Operations LLC, Houston, TX (US)

( * ) Notice: Subject to any disclaimer, the term of this patent is extended or adjusted under 35 U.S.C. 154(b) by 6 days.

(21) Appl. No.: 17/244,760

(22) Filed: Apr. 29, 2021

(65) Prior Publication Data
US 2022/0023835 A1  Jan. 27, 2022

Related U.S. Application Data

(63) Continuation-in-part of application No. 16/937,926, filed on Jul. 24, 2020, now Pat. No. 11,331,649.

(51) Int. Cl.
| | | |
|---|---|---|
| *B01J 20/34* | (2006.01) | |
| *C07D 233/02* | (2006.01) | |
| *B01D 15/20* | (2006.01) | |
| *C10G 25/12* | (2006.01) | |

(52) U.S. Cl.
CPC ........ *B01J 20/3475* (2013.01); *B01D 15/203* (2013.01); *B01J 20/3416* (2013.01); *B01J 20/3433* (2013.01); *C07D 233/02* (2013.01); *C10G 25/12* (2013.01); *C10G 2300/202* (2013.01)

(58) Field of Classification Search
None
See application file for complete search history.

(56) References Cited

U.S. PATENT DOCUMENTS

| | | | |
|---|---|---|---|
| 4,094,650 A | 6/1978 | Koh et al. | |
| 4,122,149 A | 10/1978 | Dunnery et al. | |
| 4,449,994 A | 5/1984 | Hegarty et al. | |
| 5,935,422 A | 8/1999 | Zinnen | |
| 6,406,616 B1 | 6/2002 | Rappas et al. | |
| 6,488,840 B1 | 12/2002 | Greaney et al. | |
| 6,558,533 B2 | 5/2003 | Schmidt et al. | |
| 7,128,829 B1 | 10/2006 | Kulprathipanja et al. | |
| 7,144,499 B2 | 12/2006 | Han et al. | |
| 7,186,328 B1 | 3/2007 | Schultz et al. | |
| 7,244,352 B2 | 7/2007 | Halbert et al. | |
| 7,344,686 B2 | 3/2008 | Poshusta et al. | |
| 8,142,646 B2 | 3/2012 | Choi et al. | |
| 8,562,821 B2 | 10/2013 | Nanoti et al. | |
| 9,340,808 B2 | 5/2016 | Harata et al. | |
| 2005/0173297 A1 | 8/2005 | Toida | |
| 2007/0017852 A1* | 1/2007 | Meyer | B01D 53/04 208/213 |
| 2014/0252276 A1* | 9/2014 | Chandran | B01D 53/12 96/240 |

(Continued)

FOREIGN PATENT DOCUMENTS

| | | |
|---|---|---|
| CN | 102852068 A | 1/2013 |
| CN | 102852069 A | 1/2013 |

(Continued)

OTHER PUBLICATIONS

Wang, Yuhe, et al., "Desulfurization of Liquid Fuels by Adsorption on Carbon-Based Sorbents and Ultrasound-Assisted Sorbent Regeneration", American Chemical Society, Feb. 2007, 3825-3831.

*Primary Examiner* — Tam M Nguyen
(74) *Attorney, Agent, or Firm* — Crowe & Dunlevy, P.C.

(57) ABSTRACT

A regeneration solvent comprised of one or more ethylene amines may contact an adsorbent bed that has been used to remove sulfur compounds from a hydrocarbon stream to extract adsorbed sulfur compounds from the adsorbent material in the bed to regenerate it. The one or more ethyleneamines may have structure (I), (II), or (III):

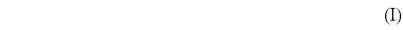

(I)

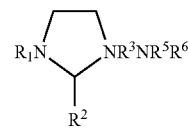

(II)

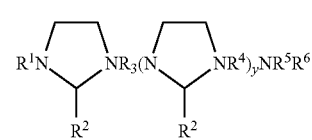

(III)

where $R^1$, $R^2$, $R^5$ and $R^6$ are, to the extent chemically possible, independently H, $C_1$-$C_4$ linear or branched alkyl, amido (RRNC=O), or hydroxyalkyl, where each R in the amido group is independently H or $C_1$ alkyl, where $R^3$ and $R^4$ are alkylene of from 1 to 4 carbon atoms, where x ranges from 0 to 3, y ranges from 1 to 6. The regenerated adsorbent bed may be reused, either alone or in combination with a liquid-liquid extraction column, to remove sulfur compounds from a hydrocarbon stream.

17 Claims, No Drawings

(56) References Cited

U.S. PATENT DOCUMENTS

| | | | |
|---|---|---|---|
| 2014/0357926 A1* | 12/2014 | Doong | C10L 3/10 |
| | | | 585/802 |
| 2015/0038759 A1 | 2/2015 | Doong et al. | |
| 2015/0225653 A1* | 8/2015 | Trucko | C10G 25/12 |
| | | | 196/46 |
| 2016/0032206 A1* | 2/2016 | Doong | C10L 3/104 |
| | | | 95/135 |
| 2018/0169561 A1 | 6/2018 | Jonnavittula et al. | |
| 2018/0296969 A1* | 10/2018 | Awadh | B01J 20/0237 |

FOREIGN PATENT DOCUMENTS

| | | |
|---|---|---|
| WO | 2008039205 A1 | 4/2008 |
| WO | 2017184591 A1 | 10/2017 |
| WO | 2018009497 A1 | 1/2018 |

* cited by examiner

ETHYLENEAMINES FOR REGENERATING ADSORBENT BEDS FOR SULFUR COMPOUND REMOVAL

CROSS-REFERENCE TO RELATED APPLICATION

This application is a continuation-in-part application from U.S. Ser. No. 16/937,926 filed Jul. 24, 2020, now U.S. Pat. No. 11,331,649, incorporated herein by reference in its entirety.

TECHNICAL FIELD

The present invention relates to methods and compounds for regenerating adsorbent beds used in removal of sulfur compounds from a hydrocarbon stream, and more particularly relates, in one non-limiting embodiment, to contacting an adsorbent bed with a regeneration solvent comprising at least one ethyleneamine to extract adsorbed sulfur compounds from the adsorbent for reuse of the bed in a further hydrocarbon stream treatment.

BACKGROUND

New U.S. regulations and international standards aimed at reducing emissions from the burning of fuels for energy are putting ever-increasing restrictions on the allowable sulfur content of finished hydrocarbon streams across the global oil and gas industry.

As part of the ongoing initiative to improve ambient air quality, the U.S. Environmental Protection Agency (EPA) in 2017 revised their gasoline standards around sulfur content from the previous Tier 2 specifications to the new Tier 3 specifications. Consequently, refineries are being forced to reduce the total sulfur content in light hydrocarbons that may be used as blend components in their finished gasoline or diesel pools.

In some cases, sulfur adsorbent beds or columns have been used to remove certain sulfur compounds, such as thiophenes, which are relatively inert and more difficult to remove, from hydrocarbon streams. However, there are feasibility issues associated with the use of adsorbent beds/columns to remove sulfur compounds from hydrocarbon streams that partly result from the limited sulfur loading capacity of these columns. Once the adsorbent column has reached maximum sulfur loading, the column either needs to be replenished with fresh adsorbent material or these columns need to be regenerated. Often the columns have to be replenished or regenerated off-site, leading to increased processing costs for refineries.

Therefore, a need exists for a developing a more cost-effective way to regenerate adsorbent beds/columns that are used for the removal of non-acidic compounds (e.g. sulfur compounds) from hydrocarbon streams.

SUMMARY

There is provided, in one form, a process for regenerating an adsorbent bed comprising adsorbed sulfur compounds, the process including contacting the adsorbent bed with an effective amount of regeneration solvent comprising one or more ethyleneamines selected from the group of ethyleneamines having structure (I), (II), or (III):

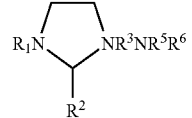
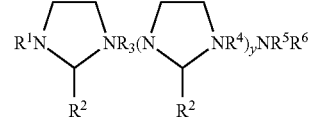

where $R^1$, $R^2$, $R^5$, and $R^6$ are, to the extent chemically possible, independently H, $C_1$-$C_4$ linear or branched alkyl, amido (RRNC=O), or hydroxyalkyl, where each R in the amido group is independently H or $C_1$ alkyl, where $R^3$ and $R^4$ are alkylene of from 1 to 4 carbon atoms, where x ranges from 0 to 3, y ranges from 1 to 6; and where the process additionally includes extracting adsorbed sulfur compounds from the adsorbent bed, wherein the adsorbent bed contains at least 5 grams of adsorbent material.

There is further provided, in another form, a process of removing sulfur compounds from a hydrocarbon stream using a regenerated adsorbent bed, the process comprising contacting a hydrocarbon stream containing sulfur compounds with a regenerated adsorbent bed, wherein the regenerated adsorbent bed contains at least 5 grams of regenerated adsorbent material, and wherein, prior to contacting with the hydrocarbon stream, the adsorbent bed is regenerated using the process described immediately above.

DETAILED DESCRIPTION

It has been discovered that a regeneration solvent composed of at least one ethyleneamine is useful and effective in extracting adsorbed sulfur species, such as thiophenes, from adsorbent materials in adsorbent beds that are employed to remove sulfur compounds from hydrocarbon streams. It has also been discovered that an adsorbent bed, which has been regenerated using such a solvent, used alone or in combination with a liquid-liquid extraction column, is effective for removing sulfur compounds from hydrocarbon streams.

In one embodiment, the regeneration solvent useful for adsorbed sulfur compound extraction from adsorbent material in an adsorbent bed comprises a carrier fluid and at least one ethyleneamine. The carrier fluid may be or include water, an alcohol, a glycol, an amide, an ester, an amine different from the ethyleneamine, a quaternary ammonium compound, and combinations thereof.

The one or more ethyleneamines may be one having structure (I), (II), or (III):

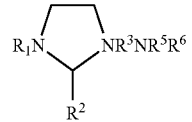
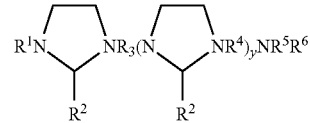

where $R^1$, $R^2$, $R^5$, and $R^6$ are, to the extent chemically possible, independently H, $C_1$-$C_4$ linear or branched alkyl, amido (RRNC=O), or hydroxyalkyl, where each R in the amido group is independently H or $C_1$ alkyl, where $R^3$ and $R^4$ are alkylene of from 1 to 4 carbon atoms, where x ranges from 0 to 3, y ranges from 1 to 6 In one non-limiting embodiment suitable ethyleneamines are those of structure (I), and more particularly are ethylene diamine, triethylenetriamine, diethylenetriamine, triethylenetetraamine, tetraethylenepentamine, and higher ethyleneamines used alone or in blends or combinations thereof.

In the regeneration solvent, the proportion of ethyleneamine in the carrier fluid can range from about 25 independently to about 100 wt %; alternatively from about 75 independently to about 99 wt %; and in another non-limiting embodiment from about 50 independently to about 74 wt %. In one non-limiting embodiment, the ethyleneamines can be used as concentrates (i.e. 100 wt %). As used herein with respect to a range, the term "independently" means that any lower threshold may be used together with any upper threshold to form a suitable alternative range.

The adsorbent bed useful in removing sulfur compounds from hydrocarbon streams that may be regenerated using the regeneration solvent of the kinds discussed herein may contain at least 5 grams of adsorbent material. The adsorbent material may be activated carbon, clay, a basic resin, silica gel, alumina, zeolites, and combinations thereof. Examples of a basic resin include, but are not necessarily limited to, polystyrene or polyacrylic polymers containing amino or ammonium substituents. In addition, these materials may be impregnated with metal ions including, but not necessarily limited to lead, copper or silver which increase their ability to remove sulfur compounds from the hydrocarbons. Further, if zeolites are used, the zeolites may be optionally impregnated with metals such as Fe, Zn, Sn and other metals.

The amount of regeneration solvent applied to or contacted with the adsorbent bed in order to properly regenerate the adsorbent material in a bed that has been used to remove sulfur compounds from a hydrocarbon stream is an amount that is effective in extracting the adsorbed sulfur compounds from the adsorbent material in the bed. The goal of contacting the regeneration solvent with the adsorbent bed is to reduce the amount of adsorbed sulfur compounds to a level that makes the adsorbent bed suitable for reuse. Complete extraction of the adsorbed sulfur compounds from the adsorbent material is desirable, but it should be appreciated that complete removal is not necessary for the methods and compounds discussed herein to be considered effective. Success is obtained if more sulfur species are removed or extracted using the solvents described herein than in the absence of an effective amount of such solvents. In one embodiment, the amount of regeneration solvent effective for extracting the adsorbed sulfur compounds from a used (i.e. spent or depleted) adsorbent bed to allow for effectual reuse of the adsorbent bed to remove sulfur species from hydrocarbon streams is at least 5 milliliters of regeneration solvent per 5 grams of adsorbent material; in another non-restrictive version at least 10 milliliters of regeneration solvent per 5 grams of adsorbent material; alternatively at least 100 milliliters of regeneration solvent per 5 grams of adsorbent material.

Alternatively, the weight ratio of solvent to absorbent may range from about 2:1 independently to about 1:2; in another non-limiting embodiment from about 2:1 independently to about 1:1, or in another non-restrictive embodiment from about 1:1 independently to about 1:2, or in a different non-limiting case about 1:1 solvent:adsorbent weight ratio.

In one non-limiting embodiment, the adsorbent bed can be regenerated at least 10 times before the adsorbent bed needs to be replaced; alternative, at least 2 times before the adsorbent bed needs to be replaced.

The regeneration of the adsorbent bed using the solvents described herein may be performed onsite, meaning that the regeneration solvent may be applied to the adsorbent bed without removing the vessel containing the adsorbent bed from the site at which it is in operation.

Once the adsorbent bed has been suitably regenerated using the solvents described herein, the resulting regenerated adsorbent bed may be used again to treat a hydrocarbon stream and help remove sulfur compounds from the hydrocarbon stream. The regenerated bed may be used alone or used in combination with a liquid-liquid extraction column to remove sulfur compounds from a hydrocarbon stream.

In one non-limiting embodiment, prior to contacting the hydrocarbon stream containing sulfur compounds with a regenerated adsorbent bed, the hydrocarbon stream containing sulfur compounds may be contacted with an extraction solvent in a separate liquid-liquid extraction column. Extraction solvents suitable for use in the liquid-liquid extraction column for removal of sulfur compounds from a hydrocarbon stream may comprise a caustic and/or a quaternary ammonium hydroxide, such as the caustics and quaternary ammonium hydroxides described above. In an exemplary but non-restrictive embodiment, the ratio of the volume of the extraction solvent to volume of the hydrocarbon stream ranges from about 100:1 to about 1:1.

The hydrocarbon stream from which sulfur compounds are removed using the adsorbent bed that is regenerated by the kinds of solvents described above and/or a liquid-liquid extraction may be any industrial hydrocarbon stream, in liquid and/or gas form, that contains sulfur compounds or sulfur species. Such streams include, but are not limited to, refinery feedstock, particularly light petroleum gases (LPG), such as (iso)butane and (iso)propane, straight run distillates, cracked stocks, hydrotreated materials, finished fuel blends, refinery fuel, flare gas, hydrogen, and possibly natural gas (which is composed mainly of methane and ethane), and/or oilfield condensate. As defined herein, LPG is composed mainly of propane and butane. The hydrocarbon stream may contain from about 1 ppm independently to about 10,000 ppm of water, more typically from about 50 ppm independently to about 1,000 ppm of water.

The sulfur compounds present in the hydrocarbon stream desired to be removed or reduced may be, without limitation, thiophenes, benzothiophenes, alkyl sulfides, alkyl disulfides, carbonyl sulfide (COS), carbon disulfide ($CS_2$), hydrogen sulfide ($H_2S$), mercaptans, and combinations thereof.

The invention will be further described with respect to the following Examples, which are not meant to limit the invention, but rather to further illustrate the various embodiments.

EXAMPLES

In a test procedure, 20 milliliter samples of an exemplary drip gas (fuel) containing about 801 ppm total sulfur and 118 ppm mercaptans (where the sulfur compounds included hydrogen sulfide, C1-C6 mercaptans, thiophenes, dialkylsulfides, and dialkyldisulfides), were passed through (1) liquid-liquid extraction columns utilizing Commercial Scavenger A or Commercial Scavenger B in a 1:1 ratio with the amount of drip gas, (2) fresh clay and/or activated carbon adsorbent beds, (3) clay and activated carbon adsorbent beds regenerated using a solution of 40 wt % triethylenetetraamine in 60 wt % water as the regeneration solvent, and (4) various combinations of these treatments to evaluate which treatments were effective in removing sulfur compounds from the drip gas samples.

Commercial Scavenger B is
Methanol 40-50 wt %
Caustic 10-20 wt %
Inorganic hydride 5-10% (in this case NaBH$_4$)
Commercial Scavenger A is
Water 40-50 wt %
Caustic 10-20 wt %
Inorganic hydride 5-10% (in this case NaBH$_4$)

Table I reflects the Total Sulfur and Mercaptan Analysis for the indicated streams. Table II presents the laboratory data for the regenerated beds. A significant difference in removal was seen when the drip gas was extracted with the ethyleneamine alone vs. adsorbent alone vs. extraction and run through an adsorbent column such as a clay or activated carbon column.

TABLE I

Total Sulfur and Mercaptan Analysis (ppm)

| Sample No. | Sample | Drip Gas (Fuel) |
|---|---|---|
| 1 | Blank (Total Sulfur) | 801 |
| 2 | Blank (Total Mercaptans) | 118 |
| | Total Sulfur Analysis | |
| 3 | Commercial Scavenger A (1:1) Extraction | 639 (20% reduction) |
| 4 | Commercial Scavenger B (1:1) Extraction | 616 (23% reduction) |
| 5 | Clay Treated | 601 (24% reduction) |
| 6 | Activated Carbon adsorption | 520 (35% reduction) |
| 7 | Clay followed by Activated Carbon adsorption | 310 (61% reduction) |
| 8 | (1:1) Extraction with Commercial Scavenger A followed by clay adsorption | 252 (68.5% reduction) |
| 9 | (1:1) Extraction with Commercial Scavenger A followed by activated carbon adsorption | 296 (63% reduction) |
| 10 | (1:1) Extraction with Commercial Scavenger A followed by clay & Activated carbon Adsorption | 158 (80% reduction) |
| 11 | (1:1) Extraction with Commercial Scavenger B followed by clay adsorption | 224 (72% reduction) |
| 12 | (1:1) Extraction with Commercial Scavenger B followed by Carbon adsorption | 248 (69% reduction) |
| 13 | (1:1) Extraction with Commercial Scavenger B followed by clay & Activated carbon adsorption | 156 (80% reduction) |

TABLE II (1:1) Extracted Fuel with Commercial Scavenger B

| Carbon Adsorbed | | Clay Adsorbed | |
|---|---|---|---|
| Cycle | % Reduction | Cycle | % Reduction |
| 1st Cycle adsorption | 69.00% | 1st Cycle adsorption | 72% |
| 2nd Cycle adsorption | 68% | 2nd Cycle adsorption | 69% |
| 3rd Cycle adsorption | 65% | 3rd Cycle adsorption | 65% |
| 4th Cycle adsorption | 59% | 4th Cycle adsorption | 69% |
| After Regeneration cycle 1 | 78% | After Regeneration cycle 1 | 69% |
| After Regeneration cycle 2 | 68% | After Regeneration cycle 2 | 66% |
| After Regeneration cycle 3 | 62% | After Regeneration cycle 3 | 63% |
| After Regeneration cycle 4 | 55% | After Regeneration cycle 4 | 61% |

In the foregoing specification, the invention has been described with reference to specific embodiments thereof. However, the specification is to be regarded in an illustrative rather than a restrictive sense. For example, hydrocarbon streams, ethyleneamines, regeneration solvents, extraction solvents, sulfur compounds, adsorbent materials, contact/extraction processes, component proportions, and separation mechanisms falling within the claimed or disclosed parameters, but not specifically identified or tried in a particular example, are expected to be within the scope of this invention.

The present invention may be practiced in the absence of an element not disclosed. In addition, the present invention may suitably comprise, consist or consist essentially of the elements disclosed. For instance, the process for regenerating an adsorbent bed may comprise, consist of, or consist essentially of: contacting an adsorbent bed with an effective amount of regeneration solvent comprising, consisting essentially of, or consisting of one or more ethyleneamines selected from the group of ethyleneamines consisting of structure (I), (II), or (III):

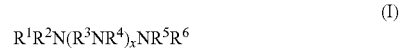

(I)

(II)

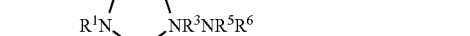

(III)

where $R^1$, $R^2$, $R^5$, and $R^6$ are, to the extent chemically possible, independently H, $C_1$-$C_4$ linear or branched alkyl, amido (RRNC=O), or hydroxyalkyl, where each R in the amido group is independently H or $C_1$ alkyl, where $R^3$ and $R^4$ are alkylene of from 1 to 4 carbon atoms, where x ranges from 0 to 3, y ranges from 1 to 6; and extracting adsorbed sulfur compounds from the adsorbent bed, wherein the adsorbent bed contains at least 5 grams of adsorbent material.

The words "comprising" and "comprises" as used throughout the claims, are to be interpreted to mean "including but not limited to" and "includes but not limited to", respectively.

To the extent used herein, the word "substantially" shall mean "being largely but not wholly that which is specified."

As used herein, the singular forms "a," "an," and "the" are intended to include the plural forms as well, unless the context clearly indicates otherwise.

As used herein, the term "about" in reference to a given parameter is inclusive of the stated value and has the meaning dictated by the context (e.g., it includes the degree of error associated with measurement of the given parameter).

As used herein, the term "and/or" includes any and all combinations of one or more of the associated listed items.

What is claimed is:

1. A process for regenerating an adsorbent bed comprising adsorbed sulfur compounds, the process comprising:
contacting the adsorbent bed with an effective amount of regeneration solvent comprising one or more ethyleneamines selected from the group of ethyleneamines consisting of structure (I), (II), or (III):

(I)

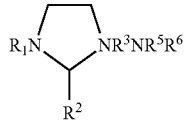

(II)

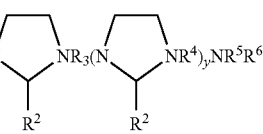

(III)

where $R^1$, $R^2$, $R^5$ and $R^6$ are, to the extent chemically possible, independently H, $C_1$-$C_4$ linear or branched alkyl, amido (RRNC=O), or hydroxyalkyl, where each R in the amido group is independently H or $C_1$ alkyl, where $R^3$ and $R^4$ are alkylene of from 1 to 4 carbon atoms, where x ranges from 0 to 3, y ranges from 1 to 6; and
extracting adsorbed sulfur compounds from the adsorbent bed, wherein the adsorbent bed contains at least 5 grams of adsorbent material.

2. The process of claim 1 where the adsorbent material in the adsorbent bed is selected from a group consisting of activated carbon, clay, a basic resin, and combinations thereof.

3. The process of claim 1 where the regeneration solvent comprises:
from about 25 to about 100 wt % of one or more ethyleneamine; and
a carrier fluid selected from the group consisting of water, an alcohol, a glycol, an amide, an ester, an amine different from the ethyleneamine, a quaternary ammonium compound, and combinations thereof.

4. The process of claim 1 where the effective amount of regeneration solvent is at least 5 milliliters of the regeneration solvent per 5 grams of adsorbent material in the adsorbent bed.

5. The process of claim 1 where, prior to contacting with the regeneration solvent, the adsorbent bed is contacted with a hydrocarbon stream containing sulfur compounds to remove sulfur compounds from the hydrocarbon stream.

6. The process of claim 1, where the adsorbed sulfur compounds are selected from a group consisting of hydrogen sulfide, mercaptans, thiophenes, benzothiophenes, alkyl sulfides, alkyl disulfides, carbonyl sulfide, carbon disulfide, and combinations thereof.

7. The process of claim 1 where the one or more ethyleneamines is selected from the group consisting of triethylenetriamine, diethylenetriamine, and combinations thereof.

8. A process for regenerating an adsorbent bed comprising adsorbed sulfur compounds, the process comprising:
contacting the adsorbent bed with a regeneration solvent comprising one or more ethyleneamines selected from the group of ethyleneamines consisting of structure (I), (II), or (III):

(I)

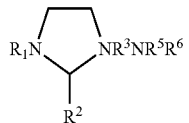

(II)

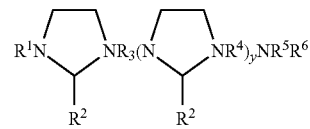

(III)

where $R^1$, $R^2$, $R^5$ and $R^6$ are, to the extent chemically possible, independently H, $C_1$-$C_4$ linear or branched alkyl, amido (RRNC=O), or hydroxyalkyl, where each R in the amido group is independently H or $C_1$ alkyl, where $R^3$ and $R^4$ are alkylene of from 1 to 4 carbon atoms, where x ranges from 0 to 3, y ranges from 1 to 6; and
extracting adsorbed sulfur compounds from the adsorbent bed, wherein the adsorbent bed contains at least 5 grams of adsorbent material;
where the amount of regeneration solvent is at least 10 milliliters of the regeneration solvent per 5 grams of adsorbent material in the adsorbent bed, and
where the adsorbed sulfur compounds are selected from a group consisting of hydrogen sulfide, mercaptans, thiophenes, benzothiophenes, alkyl sulfides, alkyl disulfides, carbonyl sulfide, carbon disulfide, and combinations thereof.

9. The process of claim 8 where the adsorbent material in the adsorbent bed is selected from a group consisting of activated carbon, clay, a basic resin, and combinations thereof.

10. The process of claim 8 where the regeneration solvent comprises:
from about 25 to about 100 wt % of one or more ethyleneamine; and
a carrier fluid selected from the group consisting of water, an alcohol, a glycol, an amide, an ester, an amine different from the ethyleneamine, a quaternary ammonium compound, and combinations thereof.

11. The process of claim 8 where, prior to contacting with the regeneration solvent, the adsorbent bed is contacted with a hydrocarbon stream containing sulfur compounds to remove sulfur compounds from the hydrocarbon stream.

12. The process of claim 8 where the one or more ethyleneamines is selected from the group consisting of triethylenetriamine, diethylenetriamine, and combinations thereof.

13. A process for regenerating an adsorbent bed comprising adsorbed sulfur compounds, the process comprising:
contacting the adsorbent bed with an effective amount of regeneration solvent, where the generation solvent comprises:
from about 25 to about 100 wt % of one or more ethyleneamine selected from the group of ethyleneamines consisting of structure (I), (II), or (III):

$$R^1R^2N(R^3NR^4)_xNR^5R^6 \quad (I)$$

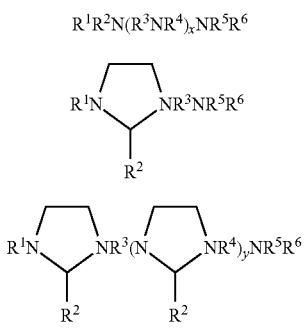

where $R^1$, $R^2$, $R^5$ and $R^6$ are, to the extent chemically possible, independently H, $C_1$-$C_4$ linear or branched alkyl, amido (RRNC=O), or hydroxyalkyl, where each R in the amido group is independently H or $C_1$ alkyl, where $R^3$ and $R^4$ are alkylene of from 1 to 4 carbon atoms, where x ranges from 0 to 3, y ranges from 1 to 6, and a carrier fluid selected from the group consisting of water, an alcohol, a glycol, an amide, an ester, an amine different from the ethyleneamine, a quaternary ammonium compound, and combinations thereof; and extracting adsorbed sulfur compounds from the adsorbent bed, wherein the adsorbent bed contains at least 5 grams of adsorbent material, where the adsorbent material in the adsorbent bed is selected from a group consisting of activated carbon, clay, a basic resin, and combinations thereof.

14. The process of claim 13 where the effective amount of regeneration solvent is at least 5 milliliters of the regeneration solvent per 5 grams of adsorbent material in the adsorbent bed.

15. The process of claim 13 where, prior to contacting with the regeneration solvent, the adsorbent bed is contacted with a hydrocarbon stream containing sulfur compounds to remove sulfur compounds from the hydrocarbon stream.

16. The process of claim 13, where the adsorbed sulfur compounds are selected from a group consisting of hydrogen sulfide, mercaptans, thiophenes, benzothiophenes, alkyl sulfides, alkyl disulfides, carbonyl sulfide, carbon disulfide, and combinations thereof.

17. The process of claim 13 where the one or more ethyleneamines is selected from the group consisting of triethylenetriamine, diethylenetriamine, and combinations thereof.

* * * * *